(12) United States Patent
Nagy et al.

(10) Patent No.: US 8,158,733 B2
(45) Date of Patent: *Apr. 17, 2012

(54) CATALYSTS BASED ON 2-(2-ARYLOXY)QUINOLINE OR 2-(2-ARYLOXY)DIHYDROQUINOLINE LIGANDS

(75) Inventors: Sandor Nagy, Naperville, IL (US); Linda N. Winslow, Cincinnati, OH (US); Shahram Mihan, Bad Soden (DE); Reynald Chevalier, Frankfurt (DE); Lenka Lukesova, Frankfurt (DE); Ilya E. Nifant'ev, Moscow (RU); Pavel V. Ivchenko, Moscow (RU)

(73) Assignee: Equistar Chemicals, LP, Houston, TX (US)

( * ) Notice: Subject to any disclaimer, the term of this patent is extended or adjusted under 35 U.S.C. 154(b) by 449 days.

This patent is subject to a terminal disclaimer.

(21) Appl. No.: 12/460,628

(22) Filed: Jul. 22, 2009

(65) Prior Publication Data

US 2011/0021727 A1    Jan. 27, 2011

(51) Int. Cl.
    C08F 4/64    (2006.01)
    C08F 4/72    (2006.01)
    C08F 4/52    (2006.01)
    B01J 31/38   (2006.01)
    C07F 7/00    (2006.01)

(52) U.S. Cl. ........ 526/172; 526/161; 526/134; 526/348; 502/103; 556/51

(58) Field of Classification Search ............ 556/51; 526/172, 161
    See application file for complete search history.

(56) References Cited

U.S. PATENT DOCUMENTS

| | | | |
|---|---|---|---|
| 5,153,157 A | 10/1992 | Hlatky et al. | |
| 5,198,401 A | 3/1993 | Turner et al. | |
| 5,241,025 A | 8/1993 | Hlatky et al. | |
| 5,414,180 A | 5/1995 | Geerts et al. | |
| 5,637,660 A * | 6/1997 | Nagy et al. | 526/160 |
| 5,648,440 A | 7/1997 | Sugano et al. | |
| 5,889,128 A | 3/1999 | Schrock et al. | |
| 6,103,657 A | 8/2000 | Murray | |
| 6,211,311 B1 | 4/2001 | Wang et al. | |
| 6,271,323 B1 | 8/2001 | Loveday et al. | |
| 6,653,417 B2 | 11/2003 | Peterson | |
| 6,706,829 B2 | 3/2004 | Boussie et al. | |
| 6,939,969 B2 | 9/2005 | Peters et al. | |
| 6,953,764 B2 | 10/2005 | Frazier et al. | |
| 7,049,378 B2 | 5/2006 | Ittel et al. | |
| 7,115,689 B2 | 10/2006 | Coalter, III et al. | |
| 7,157,400 B2 | 1/2007 | Boussie et al. | |
| 7,253,133 B2 | 8/2007 | Sun et al. | |
| 7,317,057 B2 * | 1/2008 | Solan et al. | 526/172 |
| 7,423,101 B2 | 9/2008 | Solan et al. | |
| 7,439,205 B2 | 10/2008 | Razavi et al. | |
| 7,858,718 B1 * | 12/2010 | Nagy et al. | 526/172 |
| 2005/0209420 A1 * | 9/2005 | Solan et al. | 526/172 |
| 2008/0177020 A1 | 7/2008 | Agapie et al. | |
| 2008/0182952 A1 | 7/2008 | Giesbrecht et al. | |

FOREIGN PATENT DOCUMENTS

EP    1059310 A2    12/2000

OTHER PUBLICATIONS

Ludwig et al. Z. Anorg. Allg. Chem., 1993, 619, 669-674.*
Ludwig E et al., "Complexes of Vanadium and Titanium with Salicylaldehyde Benzolyhydrazone and 2-(2'-hydroxyphenyl)-chinolin-8-olato(2) Vanadium," Zeitschrift fur Anorganische und Allgemeine Chemie, (1993), vol. 619, No. 4, 669-674.
Bei et al., "Synthesis, Structures, Bonding, and Ethylene Reactivity of Group 4 Metal Alkyl Complexes Incorporating 8-Quinolinolato Ligands," Organometallics, (1997), 16, 3283-3302.
Mao et al., "New tridentate cyclometalated platinum(II) and palladium(II) complexes of N, 2-diphenyl-8-qunolinamine: syntheses, crystal structures, and photophysical properties," Tetrahedron Letters, (2005), 46, 8419-8422.
Ittel, et al., "Late-Metal Catalysts for Ethylene Homo- and Copolymerization," Chem. Rev. 100 (2000) 1169-1203.
Agapie et al., "Zirconium and Titanium Complexes Supported by Tridentate $LX_2$ Ligands Having Two Phenolates Linked to Furan, Thiophene, and Pyridine Donors: Precatalyts for Propylene Polymerization and Oligomerization," Organometallics, (2008), 27, 6245-6256.

* cited by examiner

Primary Examiner — Rip A. Lee

(57) ABSTRACT

Catalysts useful for polymerizing olefins are disclosed. The catalysts comprise an activator and a Group 4 metal complex that incorporates a dianionic, tridentate 2-(2-aryloxy)quinoline or 2-(2-aryloxy)dihydroquinoline ligand. In one aspect, supported catalysts are prepared by first combining a boron compound having Lewis acidity with excess alumoxane to produce an activator mixture, followed by combining the activator mixture with a support and the tridentate, dianionic Group 4 metal complex. The catalysts are easy to synthesize, support, and activate, and they enable facile production of high-molecular-weight polyolefins.

14 Claims, No Drawings

US 8,158,733 B2

CATALYSTS BASED ON 2-(2-ARYLOXY)QUINOLINE OR 2-(2-ARYLOXY)DIHYDROQUINOLINE LIGANDS

FIELD OF THE INVENTION

The invention relates to non-metallocene catalysts useful for polymerizing olefins. The catalysts incorporate a tridentate dianionic ligand.

BACKGROUND OF THE INVENTION

While Ziegler-Natta catalysts are a mainstay for polyolefin manufacture, single-site (metallocene and non-metallocene) catalysts represent the industry's future. These catalysts are often more reactive than Ziegler-Natta catalysts, and they produce polymers with improved physical properties. The improved properties include controlled molecular weight distribution, reduced low molecular weight extractables, enhanced incorporation of α-olefin comonomers, lower polymer density, controlled content and distribution of long-chain branching, and modified melt rheology and relaxation characteristics.

Traditional metallocenes incorporate one or more cyclopentadienyl (Cp) or Cp-like anionic ligands such as indenyl, fluorenyl, or the like, that donate pi-electrons to the transition metal. Non-metallocene single-site catalysts, including ones that capitalize on the chelate effect, have evolved more recently. Examples are the bidentate 8-quinolinoxy or 2-pyridinoxy complexes of Nagy et al. (see U.S. Pat. No. 5,637,660), the late transition metal bisimines of Brookhart et al. (see *Chem. Rev.* 100 (2000) 1169), and the diethylenetriamine-based tridentate complexes of McConville et al. or Shrock et al. (e.g., U.S. Pat. Nos. 5,889,128 and 6,271,323).

In numerous recent examples, the bi- or tridentate complex incorporates a pyridyl ligand that bears a heteroatom β- or γ- to the 2-position of the pyridine ring. This heteroatom, typically nitrogen or oxygen, and the pyridyl nitrogen chelate the metal to form a five- or six-membered ring. For some examples, see U.S. Pat. Nos. 7,439,205; 7,423,101; 7,157,400; 6,653,417; and 6,103,657 and U.S. Pat. Appl. Publ. No. 2008/0177020. In some of these complexes, an aryl substituent at the 6-position of the pyridine ring is also available to interact with the metal through C—H activation to form a tridentate complex (see, e.g., U.S. Pat. Nos. 7,115,689; 6,953,764; 6,706,829).

Complexes in which a 2-(2-aryloxy)pyridyl group forms part of a tridentate ligand are known (see, e.g., U.S. Pat. Nos. 7,423,101; 7,049,378; and 7,253,133. U.S. Pat. Appl. Publ. No. 2008/0177020 and *Organometallics* 27 (2008) 6245 are of particular interest. They describe tridentate, dianionic complexes, including Group 4 complexes, and their use as non-metallocene catalysts for olefin polymerization. The complexes include a "linker group," most commonly phenyl, pyridyl, furanyl, or thiphenyl joins two 2-aryloxy groups. Thus, e.g., the references show bis-2,6-(2-aryloxy)pyridine complexes. Complexes in which a quinoline moiety is used as a linker are not disclosed.

Quinoline-based bi- or tridentate complexes have been described (see, e.g., U.S. Pat. Nos. 7,253,133; 7,049,378; 6,939,969; 6,103,657; 5,637,660 and *Organometallics* 16 (1997) 3282), although less frequently than their pyridyl analogs. These complexes lack a 2-(2-aryloxy)quinoline ligand and/or they are not dianionic and tridentate. U.S. Pat. No. 7,253,133 discloses numerous tridentate complexes and ligand precursors, many of which have a 2-aryloxy group. Tridentate monoanionic complexes that incorporate a pyridyl group ("A-5," col. 34) or quinolinyl group ("A-6," col. 34) are shown, and complex A-6 does not feature a 2-(2-aryloxy) quinoline ligand. Similar complexes are shown in U.S. Pat. No. 7,049,378 (see Exs. 1 and 2), both monoanionic; Example 2 shows a quinoline, but not a 2-(2-aryloxy)quinoline.

New non-metallocene catalysts useful for making polyolefins continue to be of interest. In particular, tridentate complexes that can be readily synthesized from inexpensive reagents are needed. The complexes should not be useful only in homogeneous environments; a practical complex can be supported on silica and readily activated toward olefin polymerization with alumoxanes or boron-containing cocatalysts. Ideally, the catalysts have the potential to make ethylene copolymers having high or very high molecular weights and can be utilized in high-temperature solution polymerizations.

SUMMARY OF THE INVENTION

The invention relates to catalysts useful for polymerizing olefins. The catalysts comprise an activator and a Group 4 metal complex. The complex incorporates a dianionic, tridentate 2-(2-aryloxy)quinoline or 2-(2-aryloxy)-dihydroquinoline ligand. In one aspect, a supported catalyst is prepared by first combining a boron compound having Lewis acidity with excess alumoxane to produce an activator mixture, followed by combining the activator mixture with a support and the dianionic, tridentate Group 4 metal complex. The catalysts are easy to synthesize, support, and activate, and they enable facile production of high-molecular-weight polyolefins.

DETAILED DESCRIPTION OF THE INVENTION

Catalysts of the invention are particularly useful for polymerizing olefins. They comprise an activator and a Group 4 transition metal complex. Group 4 is metals include zirconium, titanium, and hafnium. Zirconium and titanium are particularly preferred. The catalysts may include mixtures of different complexes.

The catalysts include one or more activators. The activator helps to ionize the complex and activate the catalyst. Suitable activators are well known in the art. Examples include alumoxanes (methyl alumoxane (MAO), PMAO, ethyl alumoxane, diisobutyl alumoxane), alkylaluminum compounds (triethylaluminum, diethylaluminum chloride, trimethylaluminum, triisobutylaluminum), and the like. Suitable activators include boron and aluminum compounds having Lewis acidity such as ionic borates or aluminates, organoboranes, organoboronic acids, organoborinic acids, and the like. Specific examples include lithium tetrakis(pentafluorophenyl)borate, lithium tetrakis(pentafluorophenyl)aluminate, anilinium tetrakis(pentafluorophenyl)-borate, trityl tetrakis(pentafluorophenyl)borate ("F20"), tris (pentafluorophenyl)-borane ("F15"), triphenylborane, tri-n-octylborane, bis(pentafluorophenyl)borinic acid, pentafluorophenylboronic acid, and the like. These and other suitable boron-containing activators are described in U.S. Pat. Nos. 5,153,157, 5,198,401, and 5,241,025, the teachings of which are incorporated herein by reference. Suitable activators also include aluminoboronates—reaction products of alkyl aluminum compounds and organoboronic acids—as described in U.S. Pat. Nos. 5,414,180 and 5,648,440, the teachings of which are incorporated herein by reference. Particularly preferred activators are alumoxanes, boron compounds having Lewis acidity, and mixtures thereof.

In addition to the Group 4 metal, the complex includes a dianionic, tridentate 2-(2-aryloxy)quinoline or 2-(2-aryloxy)dihydroquinoline ligand. The ligand is "tridentate" and "dianionic" in that it binds to the metal with two anionic sites and one neutral site. The neutral site is the tertiary amine group of the quinoline moiety. The anionic sites include at least one 2-aryloxy group that is attached at the 2-position of the quinoline (or dihydroquinoline) moiety. The other anionic group is normally attached at the 8-position of the quinoline ring and can incorporate any of a variety of carbon, oxygen, nitrogen, or sulfur anions. The other anionic group coordinates with the Group 4 metal to give a 5-, 6-, or 7-membered ring in the tridentate complex. Preferably, the other anionic group is an 8-anilino or an 8-(2-aryloxy) substituent.

Some preferred complexes of the invention are 2-(2-aryloxy)-8-anilinoquinolines, i.e., they have an aniline-based substituent attached at the 8-position of the quinoline ring. Particularly preferred among these are complexes that have the structure:

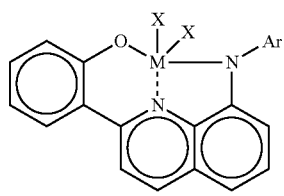

in which M is a Group 4 transition metal, Ar is an aryl group, each X is independently selected from the group consisting of halide, amide, alkyl, aryl, and alkaryl, and any of the ring carbons is optionally substituted with an alkyl, aryl, halide, alkoxy, trialkylsilyl, dialkylamino, or haloalkyl group, or any pair of adjacent ring carbons are joined to form a 5 to 7-membered carbocyclic or heterocyclic ring.

More preferred complexes of this type have the structure:

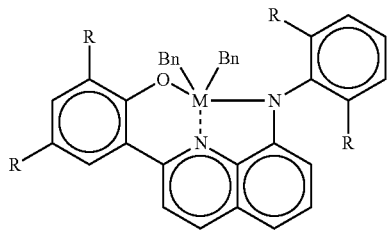

in which Bn is benzyl and each R is independently selected from the group consisting of methyl, ethyl, n-propyl, isopropyl, n-butyl, and tert-butyl.

Other preferred complexes are 2,8-bis(2-aryloxy)quinolines, i.e., they have a 2-aryloxy substitutent attached to both the 2- and 8-positions of the quinoline ring. Particularly preferred among these are complexes that have the structure:

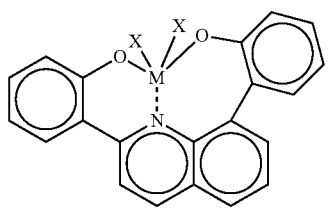

in which M is a Group 4 transition metal, each X is independently selected from the group consisting of halide, amide, alkyl, aryl, and alkaryl, and any of the ring carbons is optionally substituted with an alkyl, aryl, halide, alkoxy, trialkylsilyl, dialkylamino, or haloalkyl group, or any pair, of adjacent ring carbons are joined to form a 5 to 7-membered carbocyclic or heterocyclic ring.

Particularly preferred complexes of this type have the structure:

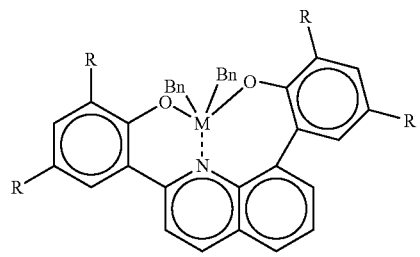

in which Bn is benzyl and each R is independently selected from the group consisting of methyl, ethyl, n-propyl, isopropyl, n-butyl, and tert-butyl.

Other preferred complexes are 2,8-bis(2-aryloxy)dihydroquinolines. Some of these complexes have the structure:

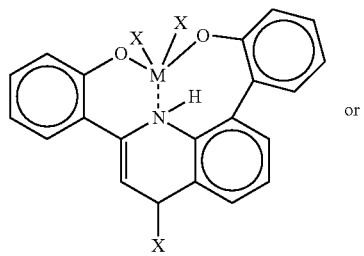

or

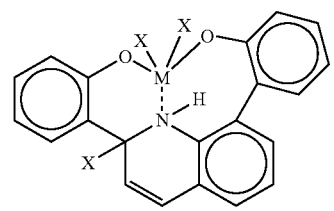

in which M is a Group 4 transition metal, each X is independently selected from the group consisting of halide, amide, alkyl, aryl, and alkaryl, and any of the ring carbons is optionally substituted with an alkyl, aryl, halide, alkoxy, trialkylsilyl, dialkylamino, or haloalkyl group, or any pair of adjacent ring carbons are joined to form a 5 to 7-membered carbocyclic or heterocyclic ring.

Particularly preferred complexes of this type have the structure:

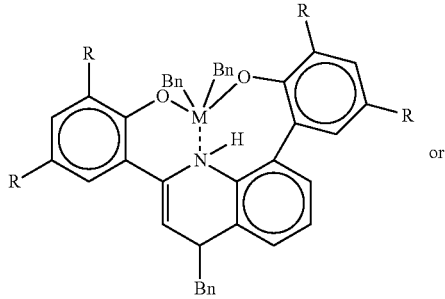

or

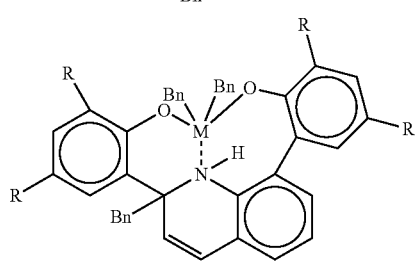

in which Bn is benzyl and each R is independently selected from the group consisting of methyl, ethyl, n-propyl, isopropyl, n-butyl, and tert-butyl.

Still other complexes are 2-(2-aryloxy)-8-arylquinolines, in which an aryl ring provides a carbanionic center to complete the tridentate structure. Preferred complexes of this type have the structure:

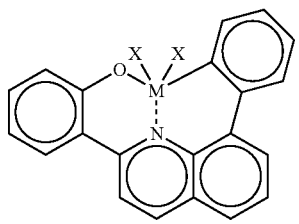

in which M is a Group 4 transition metal, each X is independently selected from the group consisting of halide, amide, alkyl, aryl, and alkaryl, and any of the ring carbons is optionally substituted with an alkyl, aryl, halide, alkoxy, trialkylsilyl, dialkylamino, or haloalkyl group, or any pair of adjacent ring carbons are joined to form a 5 to 7-membered carbocyclic or heterocyclic ring.

A few exemplary complexes:

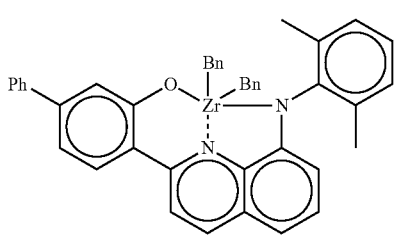

-continued

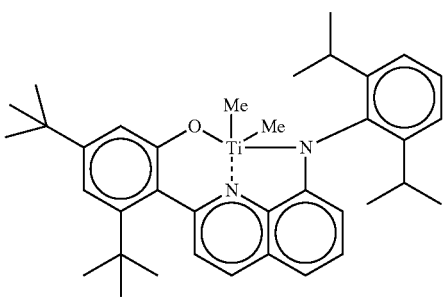

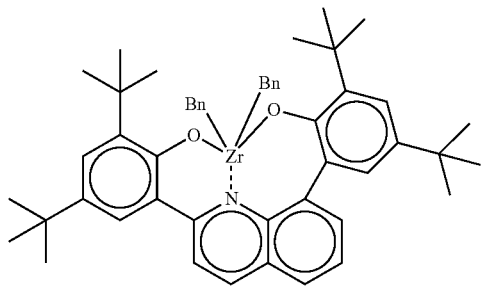

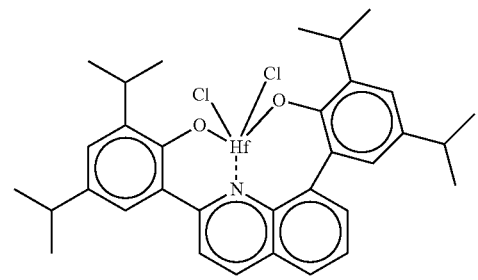

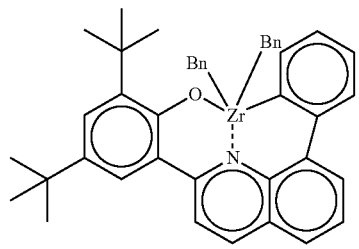

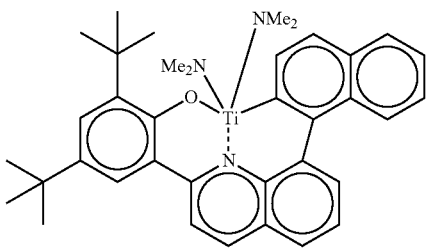

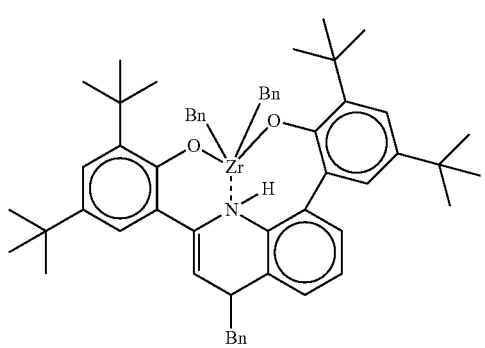

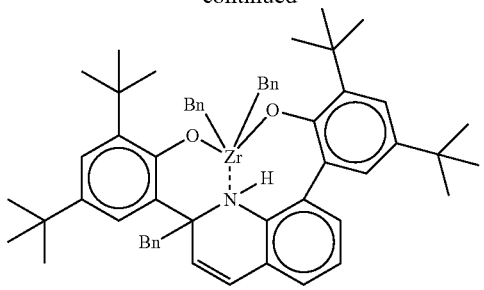

The catalysts are preferably supported on an inorganic oxide such as silica, alumina, silica-alumina, magnesia, titania, zirconia, clays, zeolites, or the Ike. Silica is preferred. When silica is used, it preferably has a surface area in the range of 10 to 1000 $m^2/g$, more preferably from 50 to 800 $m^2/g$ and most preferably from 200 to 700 $m^2/g$. Preferably, the pore volume of the silica is in the range of 0.05 to 4.0 mL/g, more preferably from 0.08 to 3.5 mL/g, and most preferably from 0.1 to 3.0 mL/g. Preferably, the average particle size of the silica is in the range of 1 to 500 microns, more preferably from 2 to 200 microns, and most preferably from 2 to 45 microns. The average pore diameter is typically in the range of 5 to 1000 angstroms, preferably 10 to 500 angstroms, and most preferably 20 to 350 angstroms.

The support is preferably treated thermally, chemically, or both prior to use by methods well known in the art to reduce the concentration of surface hydroxyl groups. Thermal treatment consists of heating (or "calcining") the support in a dry atmosphere at elevated temperature, preferably greater than 100° C., and more preferably from 150 to 800° C., prior to use. A variety of different chemical treatments can be used, including reaction with organo-aluminum, -magnesium, -silicon, or -boron compounds. See, for example, the techniques described in U.S. Pat. No. 6,211,311, the teachings of which are incorporated herein by reference.

Highly active non-metallocene catalysts of the invention can be made by using a particular sequence for activating and supporting the tridentate dianionic complexes. One method of preparing a supported catalyst useful for polymerizing olefins comprises two steps. In a first step, a boron compound having Lewis acidity (as described earlier) is combined with excess alumoxane, preferably methylalumoxane, to produce an activator mixture. In a second step, the resulting activator mixture is combined with a support, preferably silica, and a complex which comprises a Group 4 transition metal and a dianionic, tridentate 2-(2-aryloxy)quinoline or 2-(2-aryloxy) dihydroquinoline ligand. In one approach, the activator mixture is combined with the complex first, followed by the support. However, the order can be reversed; thus, the activator mixture can be combined with the support first, followed by the complex. Preferably, the ligand is a 2-(2-aryloxy)-8-anilinoquinoline, a 2,8-bis(2-aryloxy)quinoline, a 2,8-bis(2-aryloxy)dihydroquinoline, or a 2-(2-aryloxy)-8-arylquinoline.

In a typical example, the boron compound is combined with excess MAO in a minimal amount of a hydrocarbon. The complex is added and the combined mixture is then added to a large proportion of calcined silica in an incipient wetness technique to provide the supported catalyst as a free-flowing powder.

As the results in Polymerization Examples 1-3 below show, dianionic tridentate 2-(2-aryloxy)quinoline and 2-(2-aryloxy)dihydroquinoline complexes are active olefin polymerization catalysts. In particular, Method D generally provides non-metallocene catalysts with excellent activity. Compare the activity results of a supported catalyst made by Method D, Polymerization Example 2 (with complex 52) versus Method A, Polymerization Example 3 (MAO-treated silica, slurry technique, no borate). The increase in activity from Method D with these complexes is substantial and unexpected.

The invention includes processes for polymerizing olefins. In one process, at least one of ethylene, propylene, and an α-olefin is polymerized in the presence of a catalyst of the invention. Preferred α-olefins are $C_4$-$C_{20}$ α-olefins such as 1-butene, 1-hexene, 1-octene, and the like. Ethylene and mixtures of ethylene with propylene or a $C_4$-$C_{10}$ α-olefin are particularly preferred. Most preferred are polymerizations of ethylene with 1-butene, 1-hexene, 1-octene, and mixtures thereof Many types of olefin polymerization processes can be used. Preferably, the process is practiced in the liquid phase, which can include slurry, solution, suspension, or bulk processes, or a combination of these. High-pressure fluid phase or gas phase techniques can also be used. In a preferred olefin polymerization process, a supported catalyst of the invention is used. The to polymerizations can be performed over a wide temperature range, such as −30° C. to 280° C. A more preferred range is from 30° C. to 180° C.; most preferred is the range from 60° C. to 100° C. Olefin partial pressures normally range from 15 psig to 50,000 psig. More preferred is the range from 15 psig to 1000 psig.

The following examples merely illustrate the invention. Those skilled in the art will recognize many variations that are within the spirit of the invention and scope of the claims.

All intermediate compounds and complexes synthesized give satisfactory $^1$H NMR spectra consistent with the structures indicated.

Preparation of Complex 34

8-Bromo-2-(3,5-di-tert-butyl-2-methoxyphenyl) quinoline

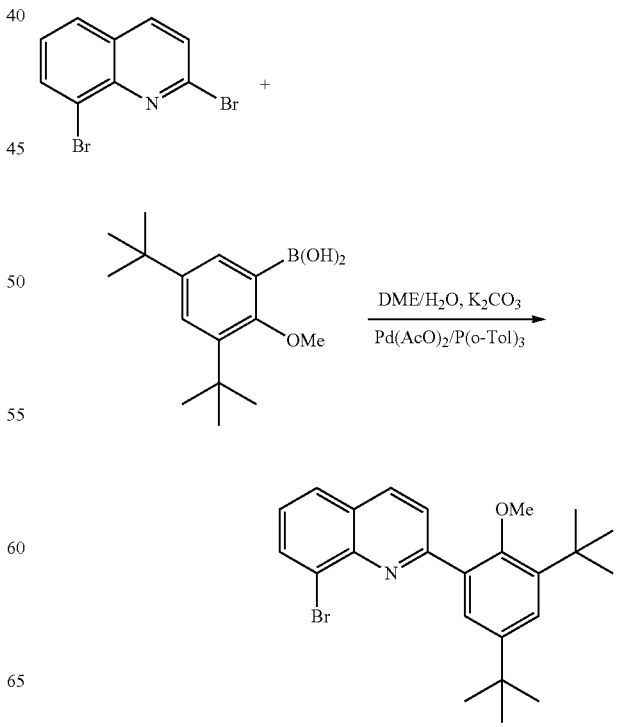

A mixture of 2,8-dibromoquinoline (4.64 g, 16 mmol, prepared by the method of L. Mao et al., *Tetrahedron Lett.* 46 (2005) 8419), 3,5-di-tert-butyl-2-methoxyphenylboronic acid (4.3 g, 16 mmol), K$_2$CO$_3$ (5.6 g, 40 mmol), Pd(OAc)$_2$ (0.08 g, 0.3 mmol), P(o-Tol)$_3$ (0.2 g, 0.6 mmol), dimethoxyethane (40 mL) and water (10 mL) is refluxed for 8 h with stirring in an argon atmosphere. The mixture is then poured into water and extracted with CHCl$_3$ (3×50 mL). The combined organic phase is washed with water and brine, and then concentrated. The residue is purified by column chromatography (silica gel 40, hexane/CH$_2$Cl$_2$ 4:1). Yield: 5.2 g (77%).

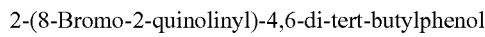

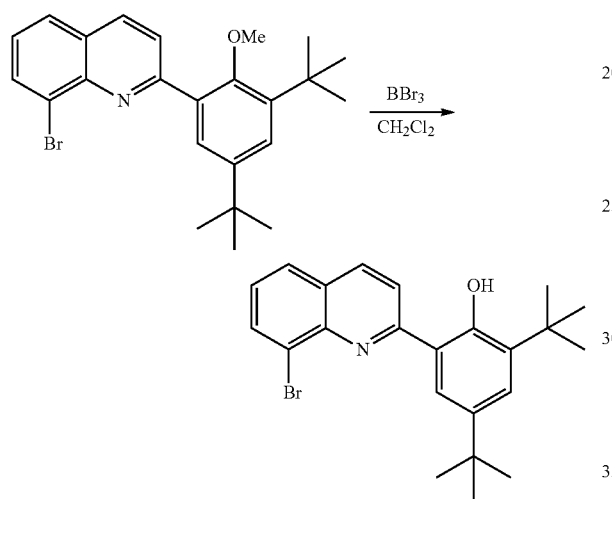

A mixture of 8-bromo-2-(3,5-di-tert-butyl-2-methoxyphenyl)quinoline (4.89 g, 11.5 mmol), BBr$_3$ (1.63 mL, 18 mmol), and CH$_2$Cl$_2$ (50 mL) is stirred for 4 h at 20° C. The reaction mixture is then diluted with cold water (100 mL). The organic phase is separated, washed with water and brine, and then to concentrated. The residue is recrystallized from hexane/benzene. Yield: 3.3 g (70%).

2,4-Di-tert-butyl-6-[8-(2,6-dimethylanilino)-2-quinolinyl]phenol

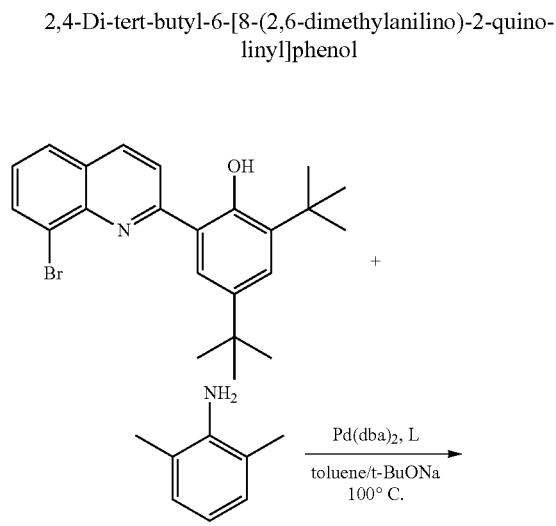

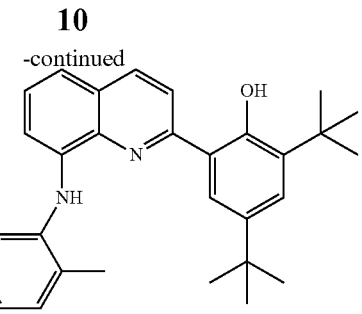

A mixture of 2-(8-bromo-2-quinolinyl)-4,6-di-tert-butylphenol (3.3 g, 8 mmol), 2,6-dimethylaniline (1.2 mL, 10 mmol), Pd(dba)$_2$ (0.036 g, 0.6 mmol), L=(N-[2'-(dicyclohexylphosphino)[1,1'-biphenyl]-2-yl]-N,N-dimethylamine) (0.05 g, 0.12 mmol), NaO$^t$Bu (0.36 g, 3.6 mmol), and toluene (8 mL) is stirred for 8 h under an argon atmosphere at 100° C. The mixture is then poured into water and extracted with benzene (3×50 mL). The combined organic phase is washed with water and brine, and is then concentrated. The residue is purified by column chromatography (silica gel 40, hexane/toluene 2:1). Yield: 2.17 g (60%).

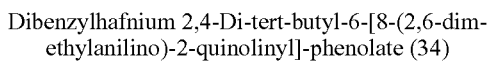

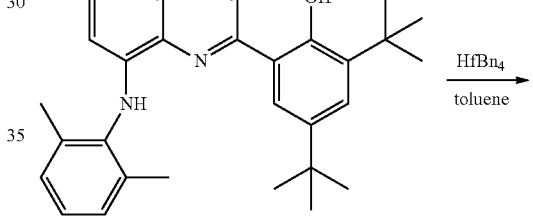

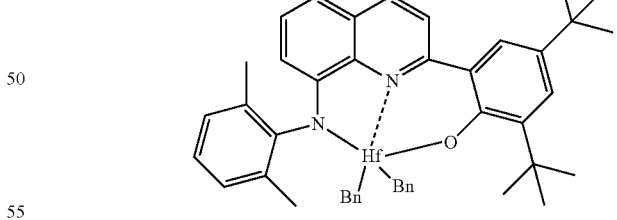

A solution of tetrabenzylhafnium (0.47 g, 0.86 mmol) in toluene (5 mL) is added at 0° C. to a solution of 2,4-di-tert-butyl-6-[8-(2,6-dimethylanilino)-2-quinolinyl]phenol (0.30 g, 0.66 mmol) in toluene (10 mL). The color of the mixture changes from pale yellow to yellow-orange. The resulting mixture is allowed to warm to room temperature and is then stirred for 8 days at 40° C. The mixture is evaporated, and pentane (20 mL) is added. The crystalline precipitate is separated by decantation, washed with pentane, and dried in vacuo. Yield of 34, a yellow crystalline powder: 0.26 g (48%).
$^1$H NMR (C$_6$D$_6$) δ: 7.74-7.66 (m, 3H); 7.45 (d, 1H); 7.22 (d, 1H); 7.15-7.13 (m, 3H); 6.99 (t, 1H); 6.79-6.62 (m, 10H); 6.18 (d, 1H); 2.40 (d, 2H); 2.31 (s, 6H); 1.97 (d, 2H); 1.75 (s, 9H); 1.36 (s, 9H).

Preparation of Complex 52

2,4-Di-tert-butyl-1-(methoxymethoxy)benzene

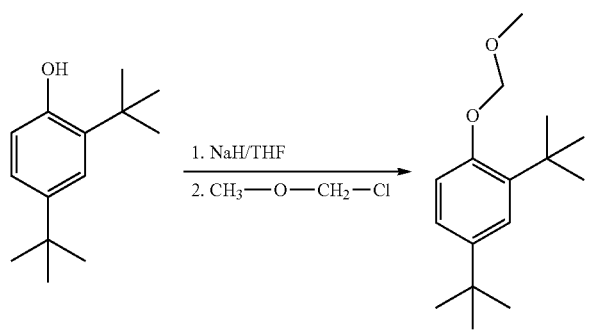

A solution of 2,4-di-tert-butylphenol (20.6 g, 0.1 mol) in dry THF (50 mL) is added with stirring to a suspension of NaH (2.4 g, 0.1 mol) in dry THF (150 mL). After 1 h of stirring, the mixture is cooled to 0° C., and chloromethyl methyl ether (7.6 mL, 0.1 mol) is added. The reaction mixture is stirred at room temperature for 2 h, quenched with water (500 mL) and extracted with Et$_2$O (2×100 mL). The combined organic phase is dried over MgSO$_4$ and evaporated under reduced pressure. The residue is used for the next step without purification.

2,8-Bis(2-methoxymethoxy-3,5-di-tert-butylphenyl)quinoline

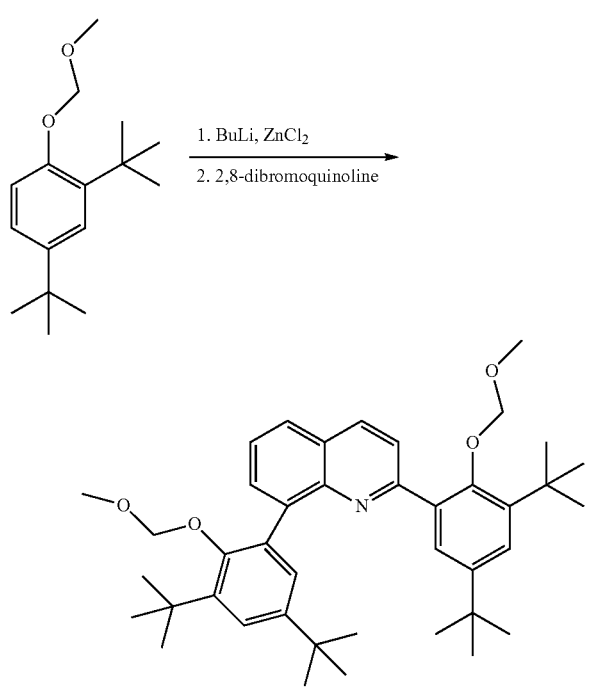

n-Butyllithium (8 mL of 2.5 M solution in hexane) is added to a solution of 2,4-di-tert-butyl-1-(methoxymethoxy)benzene (4.8 g, 19.2 mmol) in Et$_2$O (100 mL). The mixture is stirred at room temperature for 3 h. THF (80 mL) and zinc chloride (2.6 g, 19.2 mmol) are then added and stirred until the ZnCl$_2$ dissolves. After that, Pd(dba)$_2$ (0.3 g), P(o-Tol)$_3$ (0.3 g), and 2,8-dibromoquinoline (2.6 g, 9 mmol) are added. The mixture is stirred overnight, then poured into excess water and extracted with Et$_2$O (3×100 mL). The combined organic phase is dried over MgSO$_4$ and concentrated under reduced pressure. The product is purified by column chromatography (SiO$_2$, hexane/CHCl$_3$ 1:1). Yield: 2.6 g (46%).

2,8-Bis(2-hydroxy-3,5-di-tert-butylphenyl)quinoline

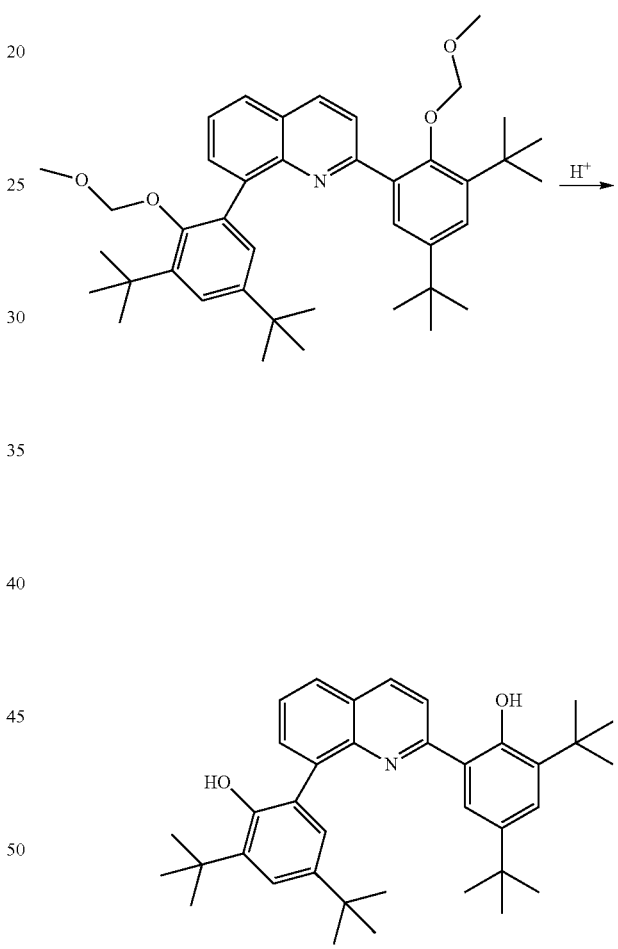

A mixture of 2,8-bis(2-methoxymethoxy-3,5-di-tert-butylphenyl)quinoline (2.6 g) and 5% aq. HCl (30 mL) is heated on a water bath for 1 h. After cooling, the product is filtered off and recrystallized from methanol. Yield: 2 g (90%). $^1$H NMR (CDCl$_3$) δ: 13.73 (br. s., 1H); 8.32 (d, 1H); 8.10 (d, 1H); 7.91 (d, 1H); 7.83 (d, 1H); 7.78 (d, 1H); 7.65 (t, 1H); 7.53 (d, 1H); 7.42 (d, 1H); 7.14 (d, 1H); 4.95 (b.s., 1H); 1.51 (s, 9H); 1.39 (s, 27H). $^{13}$C NMR (CDCl$_3$) δ: 159.4; 157.5; 149.1; 144.1; 142.4; 139.3; 137.8; 137.6; 135.9; 135.6; 132.67; 127.9;

126.9; 126.7; 126.3; 125.3; 125.0; 124.2; 121.4; 118.6; 117.9; 35.2; 35.1; 34.4; 34.3; 31.65; 31.6; 29.9; 29.5.

Dibenzylzirconium 2-benzyl-2,8-bis(3,5-di-tert-butyl-6-phenolato)-1,2-dihydroquinoline (52)

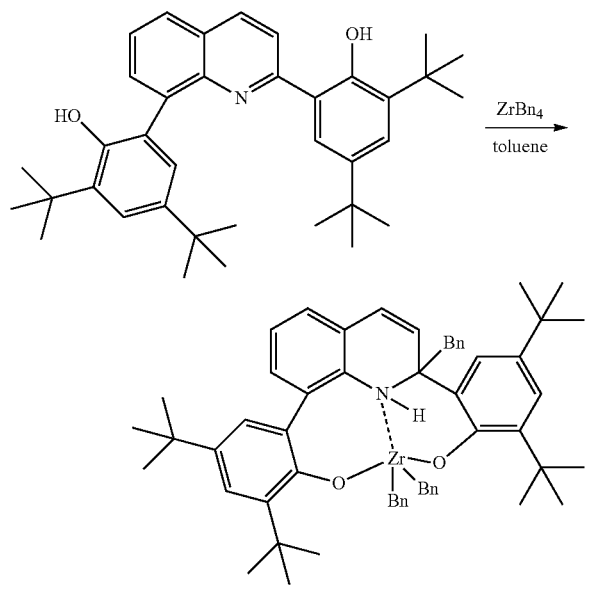

Tetrabenzylzirconium (0.46 g, 1 mmol) is added at 0° C. to a solution of 2,8-bis(2-hydroxy-3,5-di-tert-butylphenyl)quinoline (0.44 g, 0.82 mmol) in toluene (20 mL). The resulting mixture is allowed to warm to room temperature and is then stirred for 8 h at 45-50° C. The color of the mixture changes from pale yellow to yellow-orange. Toluene is evaporated and the residue is treated with hexane. A crystalline solid, the primary product, forms. This solid is recrystallized from hexane (hence the temperature of the solution reaches at least 60-70° C.), and a secondary product is isolated. Yield of 52, a yellow crystalline powder: 0.39 g (59%). The structure of 52 is confirmed by an X-ray crystal structure and $^1$H NMR spectrum of the recrystallized product.

Preparation of Supported Catalysts

Method A

A mixture of silica (Davison 948, calcined at 250° C. for 4 h, 2.0 g), methylalumoxane (30 wt.% solution of MAO in toluene, product of Albemarle, 2.2 mL), and toluene (10 mL) is stirred under nitrogen for 1 h at 80° C. The resulting slurry is cooled to ambient temperature, and a specified amount of catalyst precursor is added, dry or in toluene solution, under stirring. After 30 min., the slurry is filtered and the solids are rinsed with hexanes (2×5 mL) and dried. The resulting catalyst is used in polymerization tests.

Method D

Trityl tetrakis(pentafluorophenyl)borate (0.093 g) is added to methylalumoxane (30 wt.% solution of MAO in toluene, 2.0 mL), and the mixture is stirred for 15 min. A specified amount of complex precursor is added to the MAO/borate solution, and the mixture stirs for an additional 15 min. The resulting product is slowly added to a stirred bed of silica (Davison 948, calcined at 600° C. for 6 h, 2.0 g). The resulting free-flowing powder is used in polymerization tests.

Ethylene Polymerization

General Procedure

A dry, 2-L stainless-steel autoclave is charged with isobutane (1.0 L), triisobutylaluminum (1 M solution in hexanes, 2 mL), 1-butene (100 mL) and, optionally, hydrogen, and the contents are heated to 70° C. and pressurized with ethylene (15.5 psi partial pressure). Polymerization is started by injecting the is catalyst with a small quantity of isobutane. The temperature is maintained at 70° C., and ethylene is supplied on demand throughout the test. The reaction is terminated by cooling the reactor and venting its contents.

Polymerization Example 1

A catalyst batch is prepared using Method D and complex 34 (97.0 mg) resulting in an Al/B/Hf ratio of 77/1.2/1. A sample of catalyst corresponding to 5.0 mg of the complex is used in the polymerization test. The test yields 14.6 g of high molecular weight ethylene/butene copolymer in 70 minutes (activity: 2027 kg/mol Hf/h).

Polymerization Example 2

A catalyst batch is prepared using Method D and complex 52 (39.6 mg) resulting in an Al/B/Zr ratio of 190/1.2/1. A sample of catalyst corresponding to 5.0 mg of the complex is used in the polymerization test. The test yields 43.9 g of high molecular weight ethylene/butene copolymer in 39 minutes (activity: 10,914 kg/mol Zr/h).

Polymerization Example 3

A catalyst batch is prepared using Method A and complex 52 (75.0 mg) resulting in an Al/Zr ratio of 100/1. A sample of catalyst corresponding to 5.0 mg of the complex is used in the polymerization test. The test yields 4.1 g of high molecular weight ethylene/butene copolymer in 70 minutes (activity: 568 kg/mol Zr/h).

The preceding examples are meant only as illustrations. The following claims define the invention.

We claim:

1. A catalyst useful for polymerizing olefins, comprising an activator and a complex which comprises a Group 4 transition metal and a dianionic, tridentate 2-(2-aryloxy)quinoline or 2-(2-aryloxy)dihydroquinoline ligand.

2. The catalyst of claim 1 wherein the activator is selected from the group consisting of alumoxanes, boron compounds having Lewis acidity, and mixtures thereof.

3. The catalyst of claim 1 wherein the metal is zirconium or titanium.

4. The catalyst of claim 1 wherein the ligand is a 2-(2-aryloxy)-8-anilinoquinoline.

5. The catalyst of claim 4 wherein the complex has the structure:

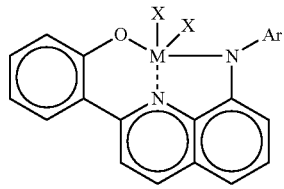

in which M is a Group 4 transition metal, Ar is an aryl group, each X is independently selected from the group consisting of halide, amide, alkyl, aryl, and alkaryl, and any of the ring carbons is optionally substituted with an alkyl, aryl, halide, alkoxy, trialkylsilyl, dialkylamino, or haloalkyl group, or any pair of adjacent ring carbons are joined to form a 5 to 7-membered carbocyclic or heterocyclic ring.

6. The catalyst of claim 5 wherein the complex has the structure:

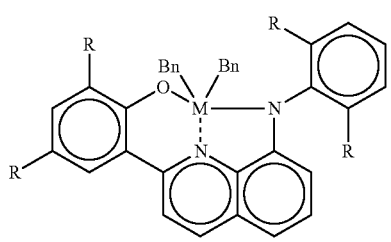

in which Bn is benzyl and each R is independently selected from the group consisting of methyl, ethyl, n-propyl, isopropyl, n-butyl, and tert-butyl.

7. The catalyst of claim 1 wherein the ligand is a 2,8-bis(2-aryloxy)quinoline or a 2,8-bis(2-aryloxy)dihydroquinoline.

8. The catalyst of claim 7 wherein the complex has the structure:

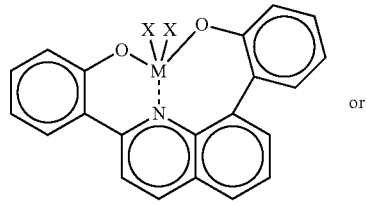

or

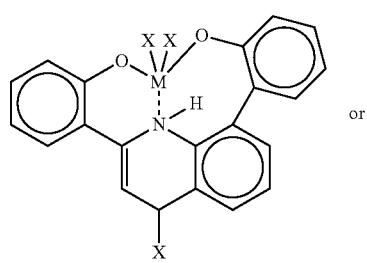

or

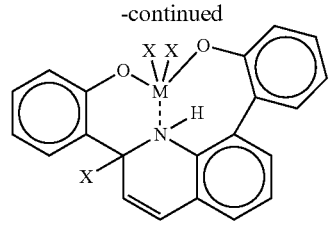

in which M is a Group 4 transition metal, each X is independently selected from the group consisting of halide, amide, alkyl, aryl, and alkaryl, and any of the ring carbons is optionally substituted with an alkyl, aryl, halide, alkoxy, trialkylsilyl, dialkylamino, or haloalkyl group, or any pair of adjacent ring carbons are joined to form a 5 to 7-membered carbocyclic or heterocyclic ring.

9. The catalyst of claim 8 wherein the complex has the structure:

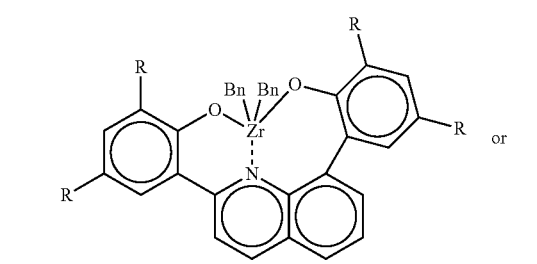 or

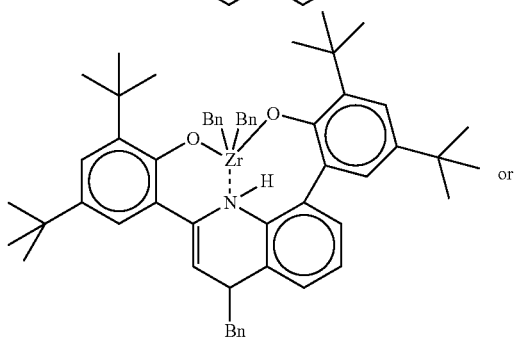 or

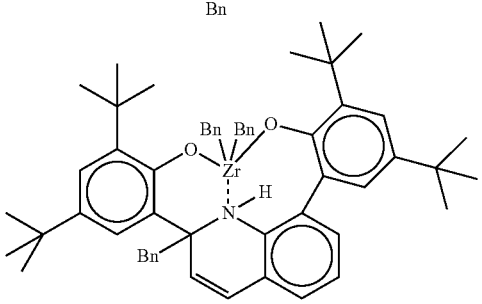

in which Bn is benzyl and each R is independently selected from the group consisting of methyl, ethyl, n-propyl, isopropyl, n-butyl, and tert-butyl.

10. The catalyst of claim 1 wherein the ligand is a 2-(2-aryloxy)-8-arylquinoline.

11. A supported catalyst of claim 1.

12. A silica-supported catalyst of claim 2.

13. A process which comprises polymerizing at least one of ethylene, propylene, and an α-olefin in the gas, solution, or slurry phase in the presence of the catalyst of claim 1.

14. The process of claim 13 wherein the α-olefin is selected from the group consisting of 1-butene, 1-hexene, 1-octene, and mixtures thereof.

* * * * *